(12) United States Patent
Bell

(10) Patent No.: US 6,376,531 B1
(45) Date of Patent: Apr. 23, 2002

(54) METHOD OF TREATMENT USING DEUTERIUM COMPOUNDS

(76) Inventor: Rupert Charles Bell, Box A, Palmer Unit, K.P.H. 1312 Oakland Dr., Kalamazoo, MI (US) 49008

( * ) Notice: Subject to any disclaimer, the term of this patent is extended or adjusted under 35 U.S.C. 154(b) by 0 days.

(21) Appl. No.: 09/439,874

(22) Filed: Nov. 12, 1999

Related U.S. Application Data

(60) Provisional application No. 60/108,377, filed on Nov. 13, 1998.

(51) Int. Cl.[7] ............ A61K 31/135; A61K 31/198; A61K 31/4045; A61K 31/405; A61K 31/4415
(52) U.S. Cl. ............ 514/418; 514/237.5; 514/345; 514/415; 514/562; 514/570; 514/653
(58) Field of Search .................. 514/237.5, 415, 514/418, 562, 570, 345, 653

(56) References Cited

U.S. PATENT DOCUMENTS

| | | | |
|---|---|---|---|
| 4,473,585 A | | 9/1984 | Abrahamsson et al. ..... 424/318 |
| 5,223,269 A | | 6/1993 | Liepins .................. 424/600 |
| 5,753,709 A | * | 5/1998 | Keavy et al. ............. 514/630 |
| 5,846,514 A | | 12/1998 | Foster et al. ............. 424/1.81 |
| 5,858,375 A | | 1/1999 | Furminger et al. ...... 424/217.1 |
| 5,895,660 A | | 4/1999 | Hoffman et al. .......... 424/449 |

OTHER PUBLICATIONS

Juorio et al., Naunym–Schmiedebergs Archives of Pharmacology, 333(3), 240–5 (Jul., 1986).*
Hayes and Palmer, Int. J. Chromobiol 4:63–69 (1976).
Dowse et al., Biol. Bull, 143: 513–524 (1972).
Hayes and Palmer, Experientia, 32/4:469–470 (1976).

* cited by examiner

Primary Examiner—Phyllis G. Spivack
(74) Attorney, Agent, or Firm—Ian C. McLeod

(57) ABSTRACT

The present invention provides organic deuterium compounds which can be therapeutic compounds to treat manic depression. In particular, the present invention relates to deuterated methionine, norepinephrine, pyridoxine-5-phosphate, tryptophan, 5-hydroxytryptophan, serotonin, N-acetyl serotonin and melatonin, which can be used as therapeutic agents.

8 Claims, 7 Drawing Sheets

METHOD OF TREATMENT USING DEUTERIUM COMPOUNDS

CROSS-REFERENCE TO RELATED APPLICATION

This application claims the benefit of U.S. Provisional Application Serial No. 60/108,377, filed Nov. 13, 1998.

STATEMENT REGARDING FEDERALLY SPONSORED RESEARCH OR DEVELOPMENT

None.

BACKGROUND OF THE INVENTION (1) Field of the Invention

The present invention relates to deuterated therapeutic compounds for the treatment of psychiatric disorders. In particular, the present invention relates to the use of deuterated tryptophan, tryptamine, serotonin, melatonin, norepinephrine, vanilmandelic acid, vanitiolide, methionine, pyridoxine-5-phosphate, and derivatives therefrom as therapeutic agents.

(2) Description of Related Art

Deuterium oxide, otherwise known as heavy water, has been to shown to have a chronomutagenic effect on the period and entrainment of the light-dark (LD) cycle of mice (Hayes and Palmer, Int. J. Chromobiol 4:63–69 (1976); and, Biol. Bull 143 513–524 (1972)). In particular, it has been shown that deuterium oxide suppressed the spontaneous locomotor activity of the mouse (Hayes and Palmer, Experientia, 4: 469–470 (1976)) Other references are Rutger Wever, In The Circadian System of Man, Springer Verlag; and, Mohammud & Sharon Shaffi, *In Phototherapy, Biological Rhythms, Mood Disorders, and the Pineal Gland,* American Psychiatric Press (1990). These cycles are also related to the manic depressive state in humans.

Lithium compounds are used for the treatment of manic depressive disorders; however, the lithium compounds are quite dosage sensitive and can be toxic to the patient at high dosages. Thus, it would be desirable to provide compounds for the treatment of these psychiatric disorders which are less dosage sensitive and toxic than lithium-based compounds.

Deuterated compounds and compositions for use in pharmaceutical applications has been the object several patents. These patents have shown that particular deuterated compounds or compositions have enhanced stability or enhanced efficacy at lower dosage levels.

U.S. Pat. No. 4,473,585 to Abrahamsson et al discloses deuterated acids, in particular perdeuterated N-hendecanoic acid or 2,2-dideutero-N-hendecanoic acid, and their use for protecting an object against attack by destructive fungi. The patent indicates that short chain compounds (citric acid) may have an undesired affect on humans.

U.S. Pat. No. 5,223,269 to Liepins discloses methods and deuterium containing compositions for treating hypertension. In particular, the compositions that are disclosed contain deuterium oxide, deuterated foods, or deuterated antihypertensive drugs.

U.S. Pat. No. 5,846,514 to Foster et al discloses a method for enhancing drug efficiency and duration of action by using drugs wherein one or more hydrogen atoms of the drug are deuterated. In particular, the method produces deuterated compounds such as nifedipine, a drug for treatment of hypertension, and penicillins.

U.S. Pat. No. 5,858,375 to Furminger et al discloses pharmaceutical compositions that consist of the drug in deuterium oxide wherein the deuterium oxide enhances the stability of the composition. In particular, the compositions relate to virus vaccines in a stabilizer consisting of deuterium oxide and other stabilizers.

U.S. Pat. No. 5,895,660 to Hoffmann et al discloses a method for enhancing the adsorption of drugs in transdermal application wherein a deuterated analogue of the drug is applied-the skin.

SUMMARY OF THE INVENTION

The present invention provides a method for treating psychiatric disorders, in particular, depression, by providing deuterated compounds to a human or animal patient. The deuterated compounds are deuterated derivatives of compounds that target the pineal gland and include such compounds as tranquilizers, basic metabolites, enzyme cofactors, specific precursors of pineal neurohormones, or neurohormonal intermediates. The deuterated compounds can be administered orally, intranasally, intravenously, or by inoculation. The preferred method is oral administration.

Therefore, the present invention provides a method of treating a depressive symptom in a human patient which comprises administering an assimilable organic deuterium compound to the patient in an amount which reduces the depressive symptoms of the patient. In particular, the patient is a manic depressive.

Further, the present invention provides a method for effecting a mental change in a human which comprises administering an effective amount of 2-hydroxy-1,2,3-trideuteropropane tricarboxylic acid which has the formula $$CH_2(COOD)CH(COOD)CH_2(COOD)$$

wherein D is a deuterium atom to the human to thereby effect the mental change in the human patient. In particular, wherein the patient is manic is depressive.

Further still, the present invention provides a method for chemically changing a biological clock of a human which comprises administering an effective amount of a non-toxic deuterated organic compound to the patient so that the biological clock is changed. This method is particularly useful when the patient is a manic depressive.

The method of the present invention further provides for one or more deuterated compounds which are selected from the group consisting of deuterated tryptophan, deuterated 5-hydroxytryptophan, deuterated serotonin, deuterated N-acetyl serotonin, deuterated melatonin, deuterated citrate, deuterated pyridoxin-5-phosphate, deuterated methionine, deuterated vanitiolide, deuterated vanilmandelic acid, deuterated norepinephrine, and deuterated derivatives thereof.

In a preferred embodiment, the deuterated tryptophan compound has the formula wherein R is a protium atom or deuterium atom and at least one R is a deuterium atom.

In a preferred embodiment, the deuterated 5-hydroxytryptophan compound has the formula

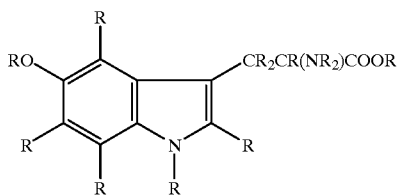

wherein R is a proton or deuterium atom and at least one R is a deuterium atom.

In a preferred embodiment, the deuterated serotonin compound has the formula

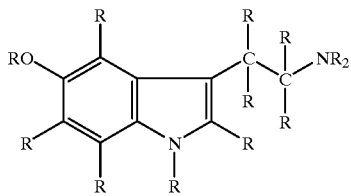

wherein R is a proton or deuterium atom and at least one R is a deuterium atom.

In a preferred embodiment, the deuterated N-acetyl serotonin compound has the formula

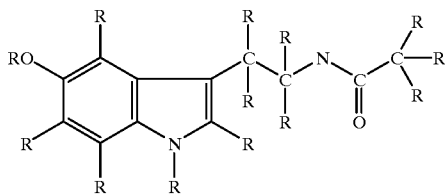

wherein R is a proton or deuterium atom and at least one R is a deuterium atom.

In a preferred embodiment, the deuterated melatonin compound has the formula

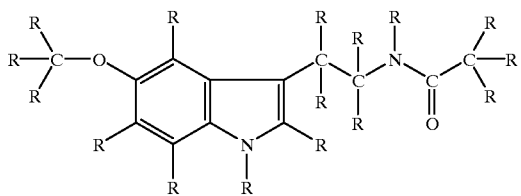

wherein R is a proton or deuterium atom and at least one R is a deuterium atom.

In a preferred embodiment, the deuterated pyridoxin-5-phosphate compound has the formula

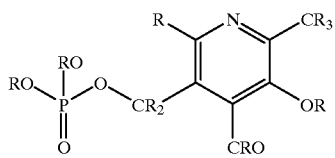

wherein R is a proton or deuterium atom and at least one R is a deuterium atom.

In a preferred embodiment, the deuterated methionine compound has the formula

wherein R is a proton or deuterium atom and at least one R is a deuterium atom.

In a preferred embodiment, the deuterated vanitiolide compound has the formula

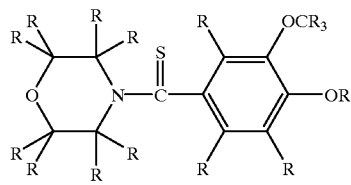

wherein R is a proton or deuterium atom and at least one R is a deuterium atom.

In a preferred embodiment, the deuterated norepinephrine compound has the formula

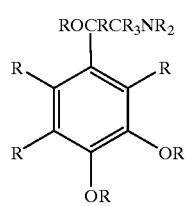

wherein R is a proton or deuterium atom and at least one R is a deuterium atom.

In a preferred embodiment, the deuterated vanilmandelic compound has the formula

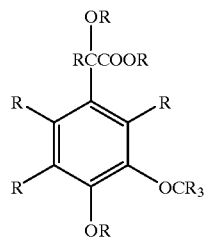

wherein R is a proton or deuterium atom and at least one R is a deuterium atom.

Methods for preparing the deuterated compounds of the present invention are also provided.

Therefore, it is an objective of the present invention to provide a method for the treatment of psychiatric disorders by administering deuterated compounds to the animal or human patient.

It is also an object of the present invention to provide compositions for the treatment of psychiatric disorders that are safer than current compounds which are used for treating psychiatric disorders.

DESCRIPTION OF PREFERRED EMBODIMENTS

Figure 1A:
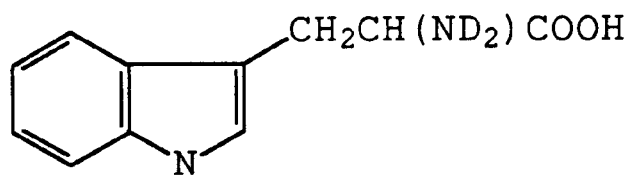
FIG. 1A is the chemical structure of a deuterated tryptophan derivative that is known as N-deuterotryptophan, alpha-dideuteroamino-1H-indole-3-propanoic acid, alpha-dideuteroamino-3-indole-3-propanoic acid, or beta-indolyl-N-alpha-dideuteroalanine.

Deuterium, or heavy hydrogen, is a stable, non-radioactive isotope of hydrogen and has an atomic weight of 2.0144. It is represented by the symbol D or $^2H$ and usually exists in the diatomic state. In nature it is a colorless and odorless gas. It is well known in the art that in the natural world hydrogen actually represents a mixture of the isotopes $^1H$ (hydrogen), D ($^2H$ or deuterium), and T ($^3H$ or tritium). Thus, all chemical compounds comprising a hydrogen (or protium) atom or proton are always present as a mixture of deuterated and non-deuterated compounds with the portion of deuterium amounting to about 0.015 mole-percent. Therefore, in the present invention, the therapeutic compound consists of a mixture wherein the percentage of the deuterated compound over the non-deuterated compound is increased in the mixture to an amount greater than 0.015 mole-percent. In a preferred embodiment of the present invention, the percent deuterium is at least 10 mole-percent and can be as much as 100 mole-percent.

As used herein, the word "proton" is the same as "hydrogen atom" or "protium atom" and is used herein to mean hydrogen atom or protium atom.

As used herein, the term "equilibrium deuteration" describes the maintenance of a particular level of deuterium in a patient by providing a sufficient amount of a deuterated compound to the patient for a predefined period of time to maintain the deuterium at a level determined to achieve the desired effect. In general, this means maintaining a ratio of the deuterated compound to its non-deuterated analogue in a patient which has been determined to produce the desired therapeutic effect.

As used herein, the term "deuterated compound" means a compound with one or more hydrogen atoms contained therein replaced with deuterium atoms. Further as used herein, the term "oligodeutero" means a compound with less than all its hydrogen atoms replaced with deuterium atoms, and the term "epideutero" means compounds wherein all the hydrogen atoms are replaced with deuterium atoms. The deuterated compounds can be made by either chemically in reactions using deuterated oxide or biologically by growing organisms such as bacteria in a deuterium oxide containing medium or plants wherein the water source is replaced by deuterium oxide.

The term "therapeutically effective amount" means those amounts that have been determined to provide the desired psychiatric effect without side effects which are considered clinically unacceptable.

Thus, the present invention provides a method for using deuterated compounds for treating psychiatric disorders such as depression, including manic depression in human and animal patients. In particular, the present invention provides a method of treating a depressive symptom in a human patient which comprises administering an assimilable organic deuterium compound to the patient in a therapeutically effective amount which reduces the depressive symptoms of the patient. Preferably, the deuterated compounds target the pineal gland.

The deuterated compounds comprise various organic compounds with all or particular protons replaced by deuterium atoms. In a preferred embodiment, the deuterated compound is selected from the group consisting of citric acid, tryptophan, methionine, norepinephrine, pyridoxine-5-phosphate, tetrahydrocannabinols, 5-hydroxytryptophan, tryptamine, benzoic acid, serotonin, and derivatives therefrom which has one or more of its hydrogen (protium) atoms replaced with deuterium atoms. The deuterated compounds can be administered to a patient in a treatment regimen to (1) increase activity of the patient, (2) decrease activity of the patient, (3) enhance normal sleep patterns in the patient, (4) accelerate the patient's circadian rhythms, (5) decelerate the patient's circadian rhythms, or (6) decrease the amplitude of activity variation in the patient's circadian rhythms. The treatment can comprise exclusively the deuterated compound or compounds or particular ratios of the deuterated compound to its non-deuterated analogues. The deuterated compounds are dispensed in capsule or tabular form in dosages that are psychologically efficacious which in particular embodiments can be 1 gram, 500 mg, 200 mg, and 100 mg doses.

The present invention also provides a method for chemically changing a biological clock of a human which comprises: administering an effective amount of a non-toxic deuterated organic compound to the patient so that the biological clock is changed. The deuterated compounds that are useful are compounds that have an effect on the biological clock and/or are compounds that are involved in biological functions that are controlled by a biological clock.

Thus, the present invention provides a variety of deuterated compounds which are useful for treating a wide range of psychiatric disorders which are either caused by pineal gland disorders or which can be controlled by altering the biological activity of the pineal gland. This can be effected equilibrium deuteration wherein a particular level of deuterium is maintained in the pineal gland. This is accomplished by providing a sufficient amount of a deuterated compound to the patient for a predefined period of time. In a preferred embodiment, the deuterated compound is derived from a compound that is known to associate with the membrane of the cells that comprise the pineal gland. The deuterated compound is readily incorporated into the cell membrane wherein it maintains a particular deuterium level in the pineal gland. The level is dependent on both the dosage of the deuterated compound and the extent the compound has been deuterated. That is the ratio of the deuterated compound to its non-deuterated analogue and/or the percent of protons per deuterium atoms per compound molecule. Thus, the patient's pineal gland can be maintained at a particular deuterium level.

The following are deuterated compounds which can be used by the method of the present invention to treat psychiatric disorders or affect the biological clock of a patient as a treatment for a psychiatric disorder.

The method provides a deuterated tryptophan compound which has the formula

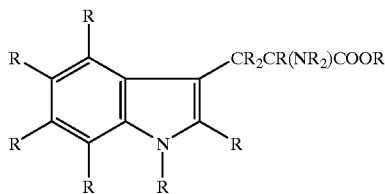

wherein R is a deuterium atom or proton and at least one R is a deuterium atom. A tryptophan compound wherein all the R are deuterium atoms is called epideutero tryptophan, and a tryptophan compound wherein at least one R is deuterium is oligodeutero tryptophan.

The deuterated tryptophan compounds can be used as tranquilizing compounds to control various psychiatric disorders such as depression. The following are particular deuterated tryptophan compounds that are contemplated by the present invention.

N-dideutero-tryptophan which has the chemical formula shown in FIG. 1A wherein D is a deuterium atom. This compound can be used as a tranquilizer which is designed to reduce the amplitude of activity changes, by slowing down the production of serotonin and melatonin.

Figure 1B:
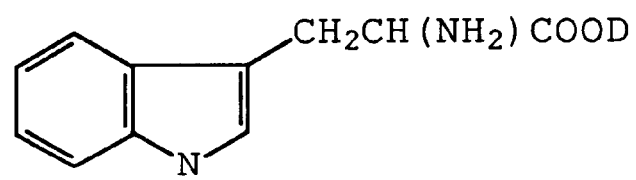
FIG. 1B is the chemical structure of a deuterated tryptophan derivative that is known as normal-tryptophan-deuterate or alpha-deuterocarboxyl-tryptamine.

Alpha-(deuterocarboxyl)-tryptamine is designed to be a psychiatric drug compound that incorporates deuterium into the pinealocytic co-enzyme system. Alpha-(deuterocarboxyl)-tryptophan has the chemical formula shown in FIG. 1B.

Figure 1C:
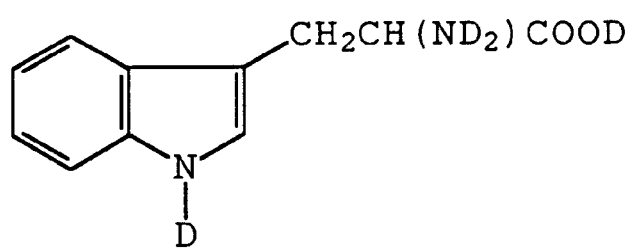
FIG. 1C is the chemical structure of a deuterated tryptophan with the hydrogen atoms in the O—H and N—H bonds replaced with deuterium atoms.

FIG. 1C shows deuterated tryptophan wherein the protons in the O—H and N—H bonds have been replaced with deuterium atoms.

Figure 2A:
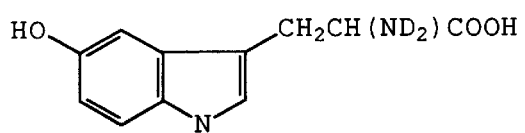
FIG. 2A is the chemical structure of a deuterated 5-hydroxytryptophan derivative that is known as 5-hydroxynaturaphan, N-dideutero-5-hydroxy-tryptophan, or 2-dideuteroamino-3-(5-hydroxyindole)-propanoic acid.
Figure 2B:
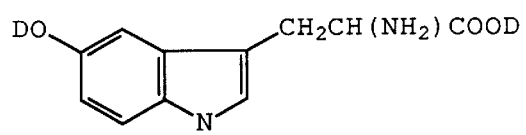
FIG. 2B is the chemical structure of a deuterated 5-hydroxytryptophan derivative that is known as 5-deuteroxy-tryptophan-deuterate or 5-deuteroxy-alpha-deuterocarboxyl-tryptamine.
Figure 2C:
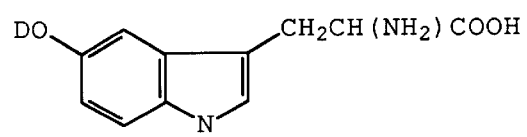
FIG. 2C is the chemical structure of a deuterated 5-hydroxytryptophan derivative that is known as 5-deuteroxy-tryptophan.
Figure 2D:
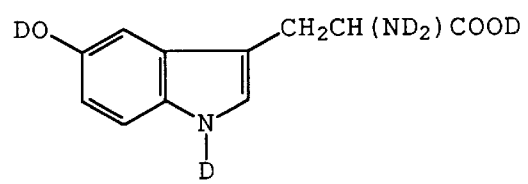
FIG. 2D is the chemical structure of a deuterated 5-hydroxytryptophan with the hydrogen atoms in the O—H and N—H bonds replaced with deuterium atoms.

The present invention also provides deuterated 5-hydroxytryptophan compounds which are useful as tranquilizing compounds. The following are examples of particular deuterated 5-hydroxytryptophan compounds. FIG. 2A shows the formula for N-deutero-5-hydroxytryptophan. FIG. 2B shows 5-deuteroxy-alpha-deuterocarboxyl-tryptophan. FIG. 2C shows 5-deuteroxytryptophan. FIG. 2D shows a deuterated 5-hydroxytryptophan wherein the protons in the O—H and N—H bonds have been replaced with deuterium atoms.

Figure 3A:
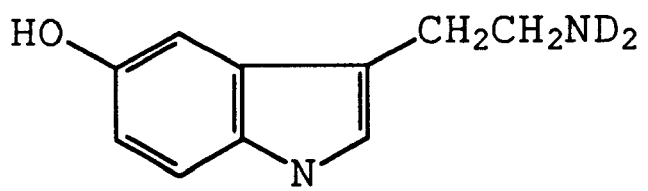
FIG. 3A is the chemical structure of a deuterated serotonin derivative that is known as N-dideutero-serotonin, N-dideutero-5-hydroxy-tryptamine, or 8-(N-dideuteroaminoethyl)-5-hydroxy-indole.
Figure 3B:
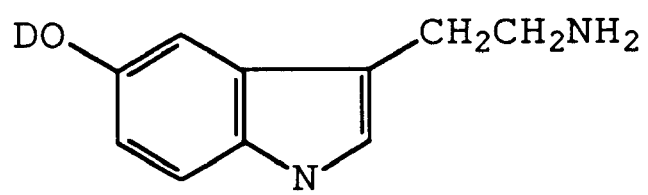
FIG. 3B is the chemical structure of a deuterated serotonin derivative that is known as 5-deuteroxy-tryptamine.
Figure 3C:
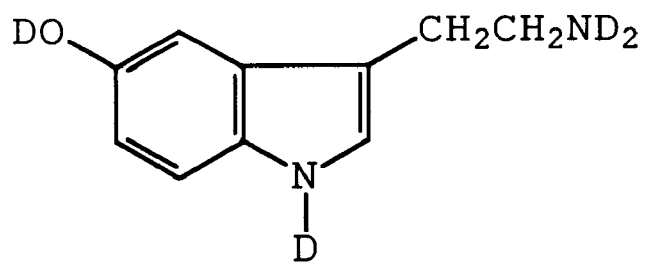
FIG. 3C is the chemical structure of a deuterated serotonin with the hydrogen atoms in the O—H and N—H bonds replaced with deuterium atoms.

The present invention further provides deuterated 5-hydroxytryptamine (serotonin) compounds which are useful as tranquilizing drugs. Serotonin is a vasoactive amine found in tissues and fluids of vertebrates and invertebrates. FIG. 3A shows N-dideutero-serotonin. FIG. 3B shows 5-deuteroxy-tryptamine. FIG. 3C shows a deuterated serotonin wherein the protons in the O—H and N—H bonds have been replaced with deuterium atoms.

Figure 4A:
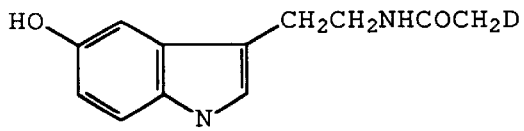
FIG. 4A is the chemical structure of a deuterated N-acetyl serotonin derivative that is known as normal-(monodeuteroacetyl)-serotonin or 5-hydroxy-N-monodeuteroacetyl)-tryptamine.
Figure 4B:
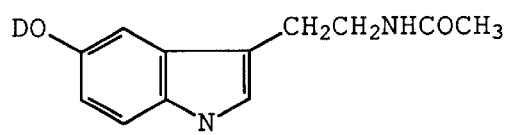
FIG. 4B is the chemical structure of a deuterated N-acetyl serotonin derivative that is known as 5-deuteroxy-normal-acetyl-tryptamine.
Figure 4C:
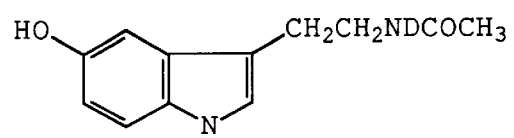
FIG. 4C is the chemical structure of a deuterated N-acetyl serotonin derivative that is known as N-monodeutero-N-acetyl-serotonin.
Figure 4D:
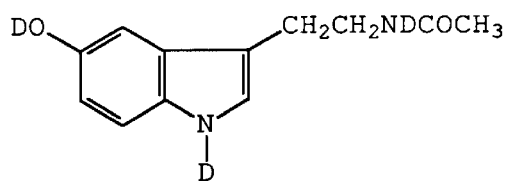
FIG. 4D is the chemical structure of a deuterated N-acetyl serotonin with the hydrogen atoms in the O—H and N—H bonds replaced with deuterium atoms.

The present invention provides further still a deuterated N-acetyl serotonin compounds which are useful as tranquilizing compounds. The following are examples of particular deuterated N-acetyl serotonin compounds. FIG. 4A shows (Monodeuteroacetyl)-serotonin. FIG. 4B shows 5-deuteroxy-acetyl-serotonin. FIG. 4C shows N-monodeutero-N-acetyl-serotonin. FIG. 4D shows a deuterated N-acetyl serotonin wherein the protons in the O—H and N—H bonds have been replaced with deuterium atoms.

Figure 5A:
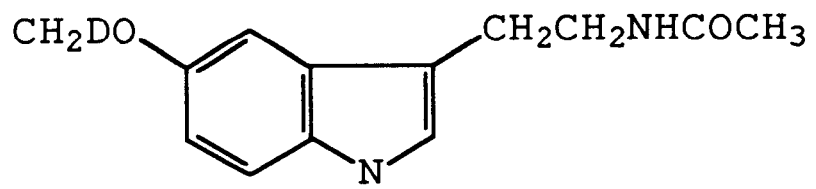
FIG. 5A is the chemical structure of a deuterated melatonin derivative that is known as 5-monodeuteromethoxy-N-acetyl-tryptamine.
Figure 5B:
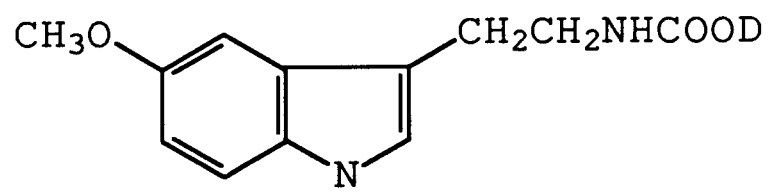
FIG. 5B is the chemical structure of a deuterated melatonin derivative that is known as 5-methoxy-N-monodeuteroacetyl-tryptamine.
Figure 5C:
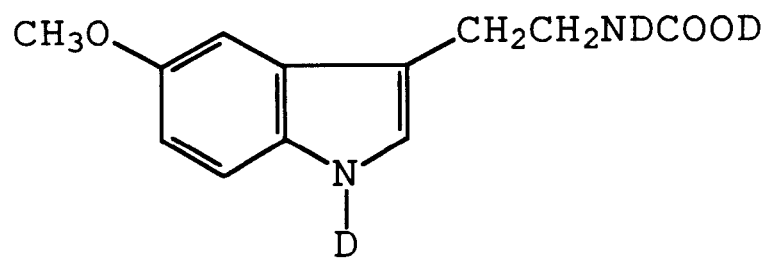
FIG. 5C is the chemical structure of a deuterated melatonin with the hydrogen atoms in the O—H and N—H bonds replaced with deuterium atoms.

Further still, the present invention provides deuterated melatonin compounds which are useful as tranquilizing drugs. Melatonin is a hormone of the pineal gland (as discussed in Axelrod and Weissbach, J. Biol. Chem. 236: 211 (1967)). FIG. 5A shows 5-monodeuteromethoxy-N-acetyl-tryptamine. FIG. 5B shows 5-methoxy-N-monodeuteroacetyl-tryptamine. FIG. 5C shows a deuterated melatonin wherein the protons in the O—H and N—H bonds have been replaced with deuterium atoms.

Figure 6A:
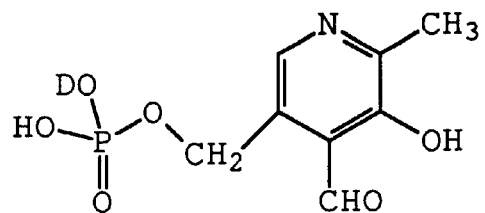
FIG. 6A is the chemical structure of a deuterated pyridoxine-5-phosphate derivative that is also known as monodeuterated pyridoxine-5-phosphate.
Figure 6B:
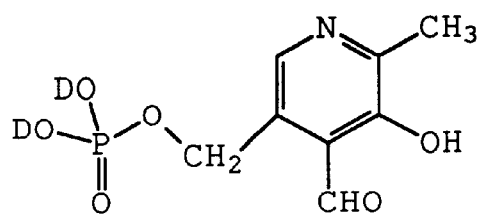
FIG. 6B is the chemical structure of a deuterated pyridoxine-5-phosphate derivative that is also known as dideuterated pyridoxine-5-phosphate.
Figure 6C:
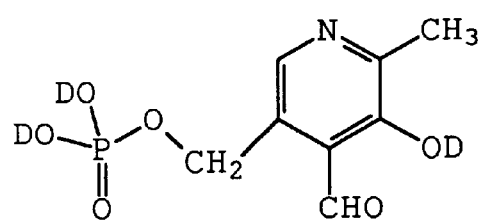
FIG. 6C is the chemical structure of a deuterated pyridoxin-5-phosphate with the hydrogen atoms in the O—H and N—H bonds replaced with deuterium atoms.

And further still, the present invention provides a deuterated pyridoxin-5-phosphate compound which has the formula shown in FIG. 6A and a dideuterated pyridoxin-5-phosphate which has the formula shown in FIG. 6B. FIG. 6C shows a deuterated pyridoxin-5-phosphate wherein the protons in the O—H bonds have been replaced with deuterium atoms. The preparation of pyridoxin-5-phosphate can be made in a reaction consisting of pyridoxal and $PCl_3O$ (phosphorus oxychloride) in $D_2O$. With the exception of $_2D$ O, the reaction is as reported by Gunsulas et al, J. Biol. Chem. 161: 743 (1945).

And further still, the present invention provides deuterated methionine compounds wherein all the protons are exchanged with deuterium atoms or compounds wherein particular protons are exchanged with deuterium atoms such as $CD_3SCH_2CH_2CH(NH_2)COOH$ or $CH_3SCH_2CH_2CH(NH_2)COOD$.

Other deuterated compounds that are useful intermediates according to the method of the present invention are 1-carboxyldeutero-methyline deuteroacetic acid and N-deutero-5-methoxy-1-deuteroacetyl-serotonin and (N,1)-deutero melatonin, respectively; 5-deuteroxy-tryptophol which has the formula

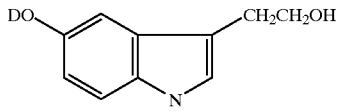

monodeuteroacetic acid ($CH_2DCOOH$); monodeuterolmethanol ($CH_2DOH$); monodeuteromethylacetate 3 ($CH_2COOH\ D$); dideuterocarbamic acid (D2NCOOH); and, monodeuterocarbamic acid (DHNCOOH). It should be understood that while particular deuterated compounds are shown herein, the present invention is not to be construed as so limited; therefore, the present invention includes deuterated compounds wherein each proton is replaced with a deuterium atom, or deuterated compounds wherein particular protons are replaced with deuterium atoms.

Figure 7A:
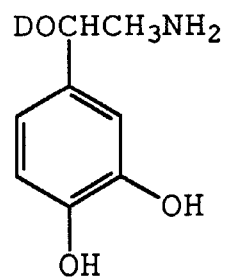
FIG. 7A is the chemical structure of a first deuterated norepinephrine derivative.
Figure 7B:
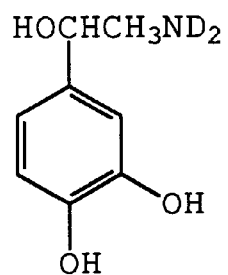
FIG. 7B is the chemical structure of a second deuterated norepinephrine derivative.
Figure 7C:
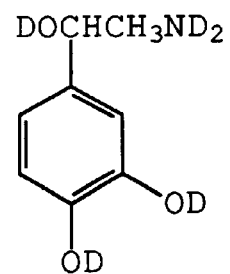
FIG. 7C is the chemical structure of a deuterated norepinephrine with the hydrogen atoms in the O—H and N—H bonds replaced with deuterium atoms.

The present invention further comprises deuterated norepinephrine wherein each proton has been replaced with a deuterium atom or the deuterated norepinephrine has the formula shown in FIG. 7A, 7B, or 7C.

The present invention further comprises deuterated derivatives of psychiatric compounds currently being used to treat psychiatric disorders. For example, the present invention comprises a deuterated vanitiolide (Merck 10071). The deuterated vanitiolide compound should be especially effective at helping people to control sudden, volatile anger, as in some borderline personalities and also perimenstrual molimina. Another useful deuterated compound is deuterated vanilmandelic acid (Merck 10070).

The present invention further comprises deuterated forms of psychoactive compounds such as tetrahydrocannabinols and yohimbine, and compounds useful as a source for deuterium for making deuterated compounds such as 1,2,3-trideuterocitrate.

The deuterated compounds used in the method of the present invention can be prepared by several alternative methods which includes chemical reactions in deuterium oxide, cultivating plants in deuterium oxide, cultivating microorganisms in deuterium oxide, and ion exchange methods which exchange deuterium atoms for protons.

A preferred deuterium-containing reagent for making deuterated therapeutic compounds of the present invention is deuterium oxide ($D_2O$) which is composed of two deuterium atoms bonded to one atom of oxygen. Deuterium oxide is commonly referred to as heavy water; however, deuterium oxide has properties that are distinct from ordinary water. Deuterium oxide is more heavily hydrogen bonded than ordinary water and as a consequence heavy water has a structure distinct from that of ordinary water.

Deuterium oxide can be used to make deuterated compounds wherein the protons in O—H and N—H bonds are exchanged for deuterium atoms in a deuterium-protium chemical exchange reaction. Generally, the compound to be deuterated is dissolved in deuterium oxide and the solution is maintained at a temperature between room temperature and boiling temperature of the deuterium oxide for several hours. Afterwards, the solution is allowed to cool and the deuterated compound is crystallized from the deuterium oxide, or in the case of compounds that do not crystallize, the deuterium oxide is removed by evaporation under a vacuum. In the case of a compound which is a solid that is not soluble in aqueous solutions such as tryptamine or is a liquid which is immiscible with aqueous solutions, the compound/deuterium mixture is stirred during the reaction to maintain intimate contact between the deuterium oxide and the compound. Compounds containing a particular ratio of deuterium to hydrogen atoms can be made in chemical reactions wherein the reaction mixture consists of a particular ratio of ordinary water and deuterium oxide. The above exchange reaction is particularly efficient in exchanging deuterium atoms for protons in the readily exchangeable O—H and N—H bonds. IR-spectra can be used to determine the efficiency of the reaction. This method has been disclosed in U.S. Pat. No. 5,895,660 to Hoffman et al which is hereby incorporated herein by reference. FIGS. 1C, 2D, 3C, 4D, 5C, 6C and 7C show deuterated tryptophan, 5-hydroxytryptophan, serotonin, N-acetyl serotonin, melatonin, pyridoxine-5-phosphate, and norepinephrine, respectively, with the protons in the N—H and O—H bonds replaced with deuterium atoms. Deuterated tryptophan, 5-hydroxytryptophan, serotonin, N-acetyl serotonin, melatonin, pyridoxine-5-phosphate, and norepinephrine which have less than all the protons in the N—H and O—H bonds replaced with deuterium atoms can also be made by the above reaction. Examples of such compounds are shown in FIGS. 1A, 1B, 2A, 2B, 2C, 3A, 3B, 4B, 4C, 5B, 6A, 6B, 7A, and 7B. In a preferred embodiment, the compounds of the present invention have the protons in the N—H and O—H bonds replaced with deuterium atoms.

A methyl exchange reaction wherein the methyl group that is to be replaced with its deuterated analogue, i.e., a $CH_3$ to $CD_3$ exchange, or a $CH_3$ to $CH_2$ exchange, is used to make deuterated compounds with deuterated methyl groups. The compound is dissolved in a mixture of deuterochloroform and deuterium oxide in a vessel, and then adding trifluoroacetic anhydride and deuteroacetone to the mixture. Then, the mixture is frozen and the vessel sealed. Next, the mixture heated at a temperature from about 50° C. to about 65° C. The mixture is maintained at the above temperature for a sufficient period of time to exchange the methyl group of the compound with the deuterated methyl group $CD_3$ or $CH_2D$. This methyl exchange method is disclosed in U.S. Pat. No. 5,846,514 to Foster et al and is hereby incorporated herein by reference. In a preferred embodiment of the present invention, each of the protons in a methyl group are replaced with deuterium atoms. In particular embodiments of the present invention, each of the protons in the methyl groups and the protons in the O—H and N—H bonds are replaced with deuterium atoms.

A method for exchanging the protons in C—H bonds in a compound with deuterium atoms can be accomplished by a protium-deuterium exchange reaction between the non-deuterated compound and deuterium oxide in the presence of deuterium-reduced Adams catalyst ($Pt$-$D_2$) which is a heterogeneous catalyst, sodium deuteroxide (NaOD) which is a homogeneous catalyst, and deuterium peroxide ($D_2O_2$) which is the promoter for the reaction. The reaction is carried out at high temperature. Typically, when the compound to be deuterated has a carboxyl group, the compound is converted to its sodium carboxylate in a salination reaction using NaOD which is the hydrolysis product of $Na_2O_2$ and $D_2O$ before performing the exchange reaction. The above reaction is disclosed in U.S. Pat. No. 4,473,585 to Abrahamsson et al and is hereby incorporated herein by reference. Afterwards, the carboxyl group is desalinated and the compound OH component of the carboxyl group can, if desired, be deuterated using the O—H exchange reaction described previously. In particular embodiments of the present invention, each of the protons in the compound, including the protons in the methyl groups and the protons in the O—H and N—H bonds are replaced with deuterium atoms.

Tryptophan which is soluble in water can be isolated from a wide variety of plants by methods well known in the art or can be synthesized in chemical reactions starting with beta-indolylaldehyde and hippuric acid, hydantoin, 3-indoleacetonitrile, or alpha-ketoglutaric acid phenylhydrazone using methods well known in the art.

Tryptamine can be isolated from plants using methods well known in the art or by synthesis starting with nitroethylene and indole using methods well known in the art. Tryptamine is practically insoluble in aqueous solutions.

5-hydroxytryptophan is a precursor of serotonin and can be synthesized from 5-benzyloxyindole and is soluble in aqueous solutions. Serotonin can be purified from tissues and fluids of vertebrates and invertebrates by methods well known in the art. Serotonin is soluble in aqueous solutions.

Melatonin which is soluble in water can be isolated from the pineal gland of beef cattle by methods well known in the art or can be synthesized from 5-methoxyindole as the starting material by methods well known in the art. Melatonin is soluble in aqueous solutions.

Norepinephrine can be synthesized by methods well known in the art to make levo and dextro forms of norepinephrine. The levo-form is freely soluble in aqueous solutions.

Methionine which is soluble in water can be synthesized from beta-methyl-mercaptoproprionaldehyde by methods well known in the art.

Various compounds of the present invention can be produced by growing organisms in deuterium oxide. The variety of organisms that can be grown in deuterium oxide consist of bacteria, molds, fungi, algae, plankton, eukaryote cells which include cells from plants, and whole plants. Brewer's yeast is a preferred source of dideuterate pyridoxal-5-phosphate.

To prepare deuterated compounds from plants, the plants are grown from seeds in the presence of an assimilable deuterium compound such as deuterium oxide so that the deuterium is incorporated into the compounds of the plant. When the only source of hydrogen for the organism is from deuterium oxide, it is expected that hydrogen atoms in each compound synthesized by the plant are replaced by a deuterium atom. The deuterated compounds are then isolated from the plant using conventional methods well known in the art for isolating the non-deuterated analogue of the deuterated compound. Deuterated compounds comprising both deuterium and protons can be prepared by growing the plants in an environment comprising a ratio of deuterium oxide and water which has been determined to produce a deuterated compound with a particular ratio of deuterium atoms to protons. As an alternative to using deuterium oxide or in addition to using deuterium oxide, deuterated citrate pellets can be used as soil additives. The deuterated citrate provides deuterium atoms to the plant via the COOD groups of the citrate molecule. Any plant that is used as a source of a compound useful for treatment of psychiatric disorders, including herbal plants used to produce compounds for the treatment of psychiatric disorders, is contemplated by the present invention.

The deuterated compounds can also be made by using microbial fermentation methods wherein microorganisms are grown in deuterium oxide or a ratio of deuterium oxide and ordinary water. The microorganisms incorporate deuterium into all the compounds manufactured by the microorganism. The ratio of deuterium to protium in the compounds can be regulated by adjusting the ratio of deuterium to hydrogen in the fermentation culture. Cultivation of microorganisms for producing the deuterated compounds is performed using methods well known in the art for cultivating microorganisms for producing the non-deuterated analogues of the deuterated compounds. Isolation of the deuterated compounds is performed using methods well known in the art for the isolation of the non-deuterated analogues of the deuterated compounds The present invention also relates to a process for the preparation of deuterated compounds which comprises: (a) providing a deuterium loaded ion exchange column; (b) introducing compound to be deuterated onto the column so that N—H and O—H hydrogen atoms are replaced with deuterium atoms; and (c) removing the deuterated compound from the column. Generally, a column is packed with a polystyrene sulfate sodium ion exchange resin such as Dowex 50 or equivalent ion exchange resin. Then the column is washed with deuteriochloric acid (deuterium chloride). Then the compound to be deuterated is passed through the column and the deuterium substituted compound is eluted from the column.

The following examples are provided to further an understanding of the present invention.

EXAMPLE 1

This example shows a method for preparing deuterated tryptophan from plants, in particular epideutero tryptophan. Pea or carrot plants are grown in soil containing potassium nitrate, potassium sulphate, potassium phosphate and potassium hydroxide (for pH regulation) fertilizer, and "watered" with deuterium oxide. For preparing oligodeutero tryptophan, the pea or carrot plants are grown in a mixture of deuterium oxide and ordinary water at a ratio that has been determined to produce the tryptophan with the desired protium to deuterium ratio.

EXAMPLE 2

This examples provides a method for preparing deuterated citrate. Citrus fruit trees, such as lemon trees, orange trees, or a tomato plant, are irrigated with deuterium oxide. The deuterated tryptophan or citrate, is then extracted from the harvested plants using standard chemical extraction techniques that are well known in the art, such as solvent partition separation, chromatography, or ion-exchange. While pea and carrot plants are good sources for tryptophan, other plants can be used for the production of tryptophan.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

I claim:

1. A method of treating a depressive symptom in a manic depressive human patient wherein the human patient is manic which comprises administering an assimilable organic deuterium compound to the patient in an amount which reduces the depressive symptom of the patient.

2. The method of claim 1 wherein the compound is selected from the group consisting of deuterated tryptophan, deuterated 5-hydroxytryptophan, deuterated serotonin, deuterated N-acetyl serotonin, deuterated melatonin, deuterated citrate, deuterated pyridoxin-5-phosphate, deuterated methionine, deuterated vanitiolide, deuterated vanilmandelic acid, and deuterated norepinephrine wherein one or more protons of the compound are replaced with deuterium atoms.

3. A method for effecting a mental change which relieves mania in a manic depressive human patient which comprises administering an effective amount of 2-hydroxy-1,2,3-trideuteropropane tricarboxylic acid which has the formula

CH$_2$(COOD)C(OH)(COOD)CH$_2$(COOD), wherein D is a deuterium atom, to the human patient to thereby effect the mental change which relieves the mania in the manic depressive human patient.

4. A method for chemically changing a biological clock of a manic depressive human which comprises administering an effective amount of a non-toxic deuterated organic compound to the patient so that the biological clock is changed in the manic depressive human.

5. The method of claim 4 wherein the non-toxic deuterated organic compound is selected from the group consisting of deuterated tryptophan, deuterated 5-hydroxytryptophan, deuterated serotonin, deuterated N-acetyl serotonin, deuterated melatonin, deuterated citrate, deuterated pyridoxin-5-phosphate, deuterated methionine, deuterated vanitiolide, deuterated vanilmandelic acid, and deuterated norepinephrine wherein one or more protons of the compound are replaced with deuterium atoms.

6. A method of treating a depressive symptom in a manic depressive human patient which comprises administering an assimilable organic deuterium compound selected from the group consisting of deuterated tryptophan, deuterated 5-hydroxytryptophan, deuterated serotonin, deuterated N-acetyl serotonin, deuterated melatonin, deuterated citrate, deuterated pyridoxin-5-phosphate, deuterated methionine, deuterated vanitiolide, deuterated vanilmandelic acid, and deuterated norepinephrine wherein one or more protons of the compound are replaced with deuterium atoms to the patient in an amount which reduces the depressive symptom of the patient.

7. A method of treating a human patient wherein the human patient is a manic depressive which comprises administering an assimilable organic deuterium compound to the patient in an amount which reduces the manic symptom or the manic symptom and depressive symptom of the patient.

8. The method of claim 7 wherein the compound is selected from the group consisting of deuterated tryptophan, deuterated 5-hydroxytryptophan, deuterated serotonin, deuterated N-acetyl serotonin, deuterated melatonin, deuterated citrate, deuterated pyridoxin-5-phosphate, deuterated methionine, deuterated vanitiolide, deuterated vanilmandelic acid, and deuterated norepinephrine wherein one or more protons of the compound are replaced with deuterium atoms.

* * * * *

UNITED STATES PATENT AND TRADEMARK OFFICE
CERTIFICATE OF CORRECTION

PATENT NO. : 6,376,531 B1
DATED : April 23, 2002
INVENTOR(S) : Rupert Charles Bell It is certified that error appears in the above-identified patent and that said Letters Patent is hereby corrected as shown below:

<u>Title page,</u>
ABSTRACT,
Lines 2 and 3, "to treat manic depression" should be -- to treat a variety of psychiatric disorders --.
Line 6, "and derivatives therefrom" should be inserted after "melatonin,".

<u>Column 3,</u>
Line 32, the structure:

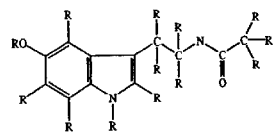

Should be as follows:

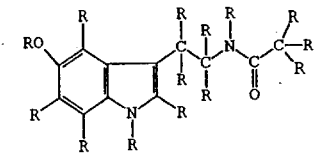

<u>Column 4,</u>
Line 63, "–3–indole–3–propanoic" should be -- –3–indolepropanoic --.

<u>Column 6,</u>
Line 38, "than ail" should be -- than all --.

UNITED STATES PATENT AND TRADEMARK OFFICE
CERTIFICATE OF CORRECTION

PATENT NO. : 6,376,531 B1
DATED : April 23, 2002
INVENTOR(S) : Rupert Charles Bell It is certified that error appears in the above-identified patent and that said Letters Patent is hereby corrected as shown below:

Column 9,
Line 14, "monodeuteromethylacetate 3" should be -- monodeuteromethylacetate $_3$ --.

Column 10,
Line 31, "$CH_3$ to $CH_2$ exchange" should be -- $CH_3$ to $CH_2$ D exchange --.

Signed and Sealed this

Twelfth Day of November, 2002

*Attest:*

*Attesting Officer*

JAMES E. ROGAN
*Director of the United States Patent and Trademark Office*